(12) United States Patent
Walch et al.

(10) Patent No.: US 11,547,572 B2
(45) Date of Patent: Jan. 10, 2023

(54) INTRA-ARTICULAR JOINT REPLACEMENT

(71) Applicant: Tornier SAS, Montbonnot-Saint-Martin (FR)

(72) Inventors: Gilles Walch, Lyons (FR); Yves-Alain Ratron, Grenoble (FR); Irene Ferrari, Le Touvet (FR); Pascal Boileau, Nice (FR)

(73) Assignee: TORNIER SAS, Montbonnot-Saint-Martin (FR)

( * ) Notice: Subject to any disclaimer, the term of this patent is extended or adjusted under 35 U.S.C. 154(b) by 0 days.

(21) Appl. No.: 14/754,506

(22) Filed: Jun. 29, 2015

(65) Prior Publication Data

US 2015/0297354 A1    Oct. 22, 2015

Related U.S. Application Data

(63) Continuation of application No. 14/069,158, filed on Oct. 31, 2013, now Pat. No. 9,089,435, which is a
(Continued)

(30) Foreign Application Priority Data

Jan. 30, 2007    (FR) ...................................... 0700622

(51) Int. Cl.
*A61B 17/17* (2006.01)
*A61F 2/40* (2006.01)
(Continued)

(52) U.S. Cl.
CPC ............ *A61F 2/40* (2013.01); *A61B 17/0401* (2013.01); *A61B 17/15* (2013.01);
(Continued)

(58) Field of Classification Search
CPC ........ A61F 2/4081; A61F 2/40; A61F 2/4014; A61F 2002/30332; A61F 2002/4085;
(Continued)

(56) References Cited

U.S. PATENT DOCUMENTS 2,666,430 A    1/1954  Gispert
3,412,733 A    11/1968 Ross
(Continued)

FOREIGN PATENT DOCUMENTS

CH        426096        12/1966
CH        507704         5/1971
(Continued)

OTHER PUBLICATIONS

Tornier Surgical Technique Addendum, Aequalis® Reversed Shoulder Polyethylene.
(Continued)

*Primary Examiner* — Ann Schillinger
(74) *Attorney, Agent, or Firm* — Duane Morris LLP

(57) ABSTRACT

A method of forming a shoulder prosthesis includes resecting an end portion of a humerus to form a resected end of the humerus and a resected portion separated from the humerus, the resected portion having an outer convex surface and an inner surface. The inner surface of the resected portion is processed to include a concave articular surface. The outer convex surface of the resected portion is implanted in the resected end of the humerus. An implant having a convex articular surface is secured to a glenoid. The concave articular surface of the resected portion is articulated with the convex articular surface of the implant.

8 Claims, 11 Drawing Sheets

Related U.S. Application Data continuation of application No. 12/787,124, filed on May 25, 2010, now Pat. No. 8,974,536, which is a continuation of application No. 12/337,385, filed on Dec. 17, 2008, now abandoned, which is a continuation-in-part of application No. 12/020,913, filed on Jan. 28, 2008, now Pat. No. 8,864,834.

(60) Provisional application No. 60/888,437, filed on Feb. 6, 2007, provisional application No. 60/971,762, filed on Sep. 12, 2007, provisional application No. 61/015,042, filed on Dec. 19, 2007.

(51) Int. Cl.

| | | |
|---|---|---|
| *A61B 17/15* | (2006.01) | |
| *A61B 17/16* | (2006.01) | |
| *A61B 17/88* | (2006.01) | |
| *A61F 2/46* | (2006.01) | |
| *A61B 17/04* | (2006.01) | |
| *A61B 17/84* | (2006.01) | |
| *A61F 2/30* | (2006.01) | |
| *A61L 27/04* | (2006.01) | |
| *A61L 27/06* | (2006.01) | |
| *A61L 27/10* | (2006.01) | |
| *A61L 27/16* | (2006.01) | |
| *A61L 27/18* | (2006.01) | |
| *A61L 27/52* | (2006.01) | |
| *A61B 17/86* | (2006.01) | |
| *A61F 2/28* | (2006.01) | |
| *A61F 2/42* | (2006.01) | |
| *A61B 17/00* | (2006.01) | |

(52) U.S. Cl.
CPC ...... *A61B 17/1684* (2013.01); *A61B 17/1739* (2013.01); *A61B 17/84* (2013.01); *A61B 17/885* (2013.01); *A61B 17/8866* (2013.01); *A61F 2/30* (2013.01); *A61F 2/4014* (2013.01); *A61F 2/4059* (2013.01); *A61F 2/4081* (2013.01); *A61F 2/4612* (2013.01); *A61F 2/4644* (2013.01); *A61L 27/042* (2013.01); *A61L 27/047* (2013.01); *A61L 27/06* (2013.01); *A61L 27/10* (2013.01); *A61L 27/16* (2013.01); *A61L 27/18* (2013.01); *A61L 27/52* (2013.01); *A61B 17/1682* (2013.01); *A61B 17/1686* (2013.01); *A61B 17/842* (2013.01); *A61B 17/86* (2013.01); *A61B 2017/00951* (2013.01); *A61F 2/28* (2013.01); *A61F 2002/3096* (2013.01); *A61F 2002/30433* (2013.01); *A61F 2002/30642* (2013.01); *A61F 2002/30754* (2013.01); *A61F 2002/30909* (2013.01); *A61F 2002/30911* (2013.01); *A61F 2002/4022* (2013.01); *A61F 2002/4062* (2013.01); *A61F 2002/4085* (2013.01); *A61F 2002/4228* (2013.01); *A61F 2002/4233* (2013.01); *A61F 2002/4243* (2013.01); *A61F 2002/4251* (2013.01); *A61F 2220/0041* (2013.01); *A61F 2310/00017* (2013.01); *A61F 2310/00023* (2013.01); *A61F 2310/00131* (2013.01); *A61F 2310/00161* (2013.01); *A61F 2310/00179* (2013.01); *A61F 2310/00359* (2013.01)

(58) Field of Classification Search
CPC .. A61F 2002/4022; A61F 2/30; A61F 2/4059; A61F 2/4612; A61F 2002/30604; A61F 2002/4018
See application file for complete search history.

(56) References Cited

U.S. PATENT DOCUMENTS

| | | |
|---|---|---|
| 3,694,820 A | 10/1972 | Scales |
| 3,815,157 A | 6/1974 | Skorecki et al. |
| 3,842,442 A | 10/1974 | Kolbel |
| 3,864,758 A | 2/1975 | Yakich |
| 3,869,730 A | 3/1975 | Skobel |
| 3,916,451 A | 11/1975 | Buechel et al. |
| 3,938,198 A * | 2/1976 | Kahn .................. A61L 27/34 623/22.15 |
| 3,978,528 A | 9/1976 | Buechel et al. |
| 3,979,778 A | 9/1976 | Stroot |
| 3,992,726 A | 11/1976 | Freeman et al. |
| 4,003,095 A | 1/1977 | Gristina |
| 4,023,572 A | 5/1977 | Weigand et al. |
| 4,030,143 A | 6/1977 | Elloy et al. |
| 4,040,131 A | 8/1977 | Gristina |
| 4,042,980 A | 8/1977 | Swanson et al. |
| 4,054,955 A | 10/1977 | Seppo |
| 4,126,924 A | 11/1978 | Akins et al. |
| 4,131,116 A | 12/1978 | Hendrick |
| 4,135,517 A | 1/1979 | Reale |
| 4,179,758 A | 12/1979 | Gristina |
| 4,206,517 A | 6/1980 | Pappas |
| 4,261,062 A | 4/1981 | Amstutz |
| 4,406,023 A | 9/1983 | Harris |
| 4,479,271 A | 10/1984 | Bolesky et al. |
| 4,550,450 A | 11/1985 | Kinnett |
| 4,623,353 A | 11/1986 | Buechel et al. |
| 4,632,111 A | 12/1986 | Roche |
| 4,662,891 A | 5/1987 | Noiles |
| 4,693,723 A | 9/1987 | Gabard |
| 4,743,262 A | 5/1988 | Tronzo |
| 4,822,370 A | 4/1989 | Schelhas |
| 4,846,840 A | 7/1989 | Leclercq et al. |
| 4,865,605 A | 9/1989 | Dines et al. |
| 4,865,609 A | 9/1989 | Roche |
| 4,883,491 A | 11/1989 | Mallory et al. |
| 4,892,549 A | 1/1990 | Figgie, III et al. |
| 4,919,670 A | 4/1990 | Dale et al. |
| 4,957,510 A | 9/1990 | Cremascoli |
| 4,963,155 A | 10/1990 | Lazzer et al. |
| 4,964,865 A | 10/1990 | Burkhead et al. |
| 4,986,833 A | 1/1991 | Worland |
| 5,030,233 A * | 7/1991 | Ducheyne .......... A61F 2/30907 623/23.54 |
| 5,032,132 A | 7/1991 | Matsen, III et al. |
| 5,053,050 A | 10/1991 | Italy |
| 5,080,673 A | 1/1992 | Burkhead et al. |
| 5,080,685 A | 1/1992 | Bolesky et al. |
| 5,127,920 A | 7/1992 | MacArthur |
| 5,135,529 A | 8/1992 | Paxson et al. |
| 5,163,961 A | 11/1992 | Harwin |
| 5,163,964 A | 11/1992 | Lazzeri et al. |
| 5,171,277 A | 12/1992 | Roger |
| 5,181,928 A | 1/1993 | Bolesky et al. |
| 5,192,329 A | 3/1993 | Christie et al. |
| 5,201,882 A | 4/1993 | Paxson |
| 5,206,925 A | 4/1993 | Nakazawa et al. |
| 5,222,984 A | 6/1993 | Forte |
| 5,257,995 A | 11/1993 | Umber et al. |
| 5,261,914 A | 11/1993 | Warren |
| 5,282,865 A | 2/1994 | Dong |
| 5,314,479 A | 5/1994 | Rockwood et al. |
| 5,314,487 A | 5/1994 | Schryver et al. |
| 5,330,531 A | 7/1994 | Capanna |
| 5,358,526 A | 10/1994 | Tornier |
| 5,383,936 A | 1/1995 | Kubein et al. |
| 5,425,779 A | 6/1995 | Schlosser et al. |
| 5,435,722 A | 7/1995 | Mandell |
| 5,443,515 A | 8/1995 | Cohen et al. |
| 5,443,519 A | 8/1995 | Averill et al. |
| 5,462,563 A | 10/1995 | Shearer et al. |
| 5,489,309 A | 2/1996 | Lackey et al. |
| 5,489,310 A | 2/1996 | Mikhail |
| 5,507,817 A | 4/1996 | Craig et al. |
| 5,507,818 A | 4/1996 | McLaughlin |

(56) References Cited

U.S. PATENT DOCUMENTS

| | | | |
|---|---|---|---|
| 5,507,819 A * | 4/1996 | Wolf | A61F 2/4081 623/19.11 |
| 5,507,824 A | 4/1996 | Lennox | |
| 5,534,033 A * | 7/1996 | Simpson | A61F 2/30721 623/13.14 |
| 5,540,697 A | 7/1996 | Rehmann et al. | |
| 5,549,682 A | 8/1996 | Roy | |
| 5,571,203 A * | 11/1996 | Masini | A61F 2/30739 623/22.46 |
| 5,580,352 A | 12/1996 | Sekel | |
| 5,702,447 A | 12/1997 | Walch | |
| 5,702,457 A | 12/1997 | Walch | |
| 5,702,486 A | 12/1997 | Craig | |
| 5,723,018 A | 3/1998 | Cyprien et al. | |
| 5,728,161 A | 3/1998 | Camino et al. | |
| 5,741,335 A | 4/1998 | Gerber et al. | |
| 5,755,719 A | 5/1998 | Frieze et al. | |
| 5,755,807 A | 5/1998 | Anstaett et al. | |
| 5,776,194 A | 7/1998 | Mikol et al. | |
| 5,779,709 A | 7/1998 | Harris, Jr. et al. | |
| 5,800,551 A | 9/1998 | Williamson et al. | |
| 5,800,557 A | 9/1998 | Elhami | |
| 5,879,355 A | 3/1999 | Ullmark | |
| 5,879,405 A | 3/1999 | Ries et al. | |
| 5,902,340 A | 5/1999 | White et al. | |
| 5,910,171 A | 6/1999 | Kummer et al. | |
| 5,928,285 A | 7/1999 | Bigliani et al. | |
| 5,941,706 A | 8/1999 | Ura | |
| 5,944,758 A | 8/1999 | Mansat et al. | |
| 5,954,727 A | 9/1999 | Collazo | |
| 5,961,555 A | 10/1999 | Huebner | |
| 5,972,368 A | 10/1999 | McKay | |
| 5,984,927 A | 11/1999 | Wenstrom et al. | |
| 6,015,437 A | 1/2000 | Stossel | |
| 6,027,503 A | 2/2000 | Khalili et al. | |
| 6,033,439 A | 3/2000 | Camino et al. | |
| 6,045,302 A | 4/2000 | Orr | |
| 6,045,582 A | 4/2000 | Prybyla | |
| 6,045,583 A | 4/2000 | Gross et al. | |
| 6,090,145 A | 7/2000 | Hassler et al. | |
| 6,096,084 A * | 8/2000 | Townley | A61F 2/32 623/23.14 |
| 6,102,953 A | 8/2000 | Huebner | |
| 6,129,764 A | 10/2000 | Servidio | |
| 6,146,423 A | 11/2000 | Cohen et al. | |
| 6,165,224 A | 12/2000 | Tornier | |
| 6,171,341 B1 | 1/2001 | Boileau et al. | |
| 6,174,335 B1 | 1/2001 | Varieur et al. | |
| 6,187,012 B1 | 2/2001 | Masini | |
| 6,197,062 B1 | 3/2001 | Fenlin | |
| 6,197,063 B1 | 3/2001 | Dews | |
| 6,203,575 B1 | 3/2001 | Farey | |
| 6,206,925 B1 | 3/2001 | Tornier | |
| 6,221,076 B1 | 4/2001 | Albrektsson et al. | |
| 6,228,120 B1 | 5/2001 | Leonard et al. | |
| 6,245,074 B1 | 6/2001 | Allard et al. | |
| 6,264,299 B1 | 7/2001 | Noda | |
| 6,267,767 B1 | 7/2001 | Strobel et al. | |
| 6,283,999 B1 | 9/2001 | Rockwood | |
| 6,306,171 B1 | 10/2001 | Conzemius | |
| 6,312,467 B1 | 11/2001 | McGee | |
| 6,334,874 B1 | 1/2002 | Tornier et al. | |
| 6,364,910 B1 | 4/2002 | Shultz et al. | |
| 6,368,271 B1 | 4/2002 | Sharratt | |
| 6,368,352 B1 | 4/2002 | Camino et al. | |
| 6,368,353 B1 | 4/2002 | Arcand | |
| 6,379,917 B1 | 4/2002 | Okun et al. | |
| 6,383,227 B1 * | 5/2002 | Baroud | A61F 2/3601 623/23.22 |
| 6,398,812 B1 | 6/2002 | Masini | |
| 6,406,495 B1 | 6/2002 | Schoch | |
| 6,406,496 B1 | 6/2002 | Rüter | |
| 6,409,730 B1 | 6/2002 | Green et al. | |
| 6,436,144 B1 | 8/2002 | Ahrens | |
| 6,436,146 B1 | 8/2002 | Hassler et al. | |
| 6,436,147 B1 | 8/2002 | Zweymüller | |
| 6,454,811 B1 | 9/2002 | Sherwood et al. | |
| 6,458,136 B1 | 10/2002 | Allard et al. | |
| 6,475,221 B1 | 11/2002 | White et al. | |
| 6,475,243 B1 | 11/2002 | Sheldon et al. | |
| 6,494,913 B1 | 12/2002 | Huebner | |
| 6,506,214 B1 | 1/2003 | Gross | |
| 6,508,840 B1 | 1/2003 | Rockwood et al. | |
| 6,511,511 B1 | 1/2003 | Slivka et al. | |
| 6,514,287 B2 | 2/2003 | Ondrla et al. | |
| 6,520,994 B2 | 2/2003 | Nogarin | |
| 6,530,957 B1 | 3/2003 | Jack | |
| 6,541,022 B1 | 4/2003 | Murphy et al. | |
| 6,558,428 B2 | 5/2003 | Rockwood | |
| 6,569,202 B2 | 5/2003 | Whiteside | |
| 6,589,281 B2 | 7/2003 | Hyde | |
| 6,605,117 B2 | 8/2003 | Kuberasampath et al. | |
| 6,620,197 B2 | 9/2003 | Maroney et al. | |
| 6,626,946 B1 | 9/2003 | Walch et al. | |
| 6,673,114 B2 | 1/2004 | Hartdegen | |
| 6,673,115 B2 | 1/2004 | Resch et al. | |
| 6,679,916 B1 | 1/2004 | Frankle et al. | |
| 6,692,563 B2 | 2/2004 | Zimmermann | |
| 6,730,252 B1 | 5/2004 | Teoh et al. | |
| 6,736,851 B2 | 5/2004 | Maroney et al. | |
| 6,746,452 B2 | 6/2004 | Tuke et al. | |
| 6,746,487 B2 | 6/2004 | Seifert et al. | |
| 6,749,637 B1 | 6/2004 | Bähler | |
| 6,755,866 B2 | 6/2004 | Southworth | |
| 6,761,740 B2 | 7/2004 | Tornier | |
| 6,767,928 B1 | 7/2004 | Murphy et al. | |
| 6,780,190 B2 | 8/2004 | Maroney | |
| 6,783,549 B1 | 8/2004 | Stone et al. | |
| 6,790,234 B1 * | 9/2004 | Frankle | A61F 2/40 623/19.12 |
| 6,797,006 B2 | 9/2004 | Hodorek | |
| 6,863,690 B2 | 3/2005 | Ball | |
| 6,875,234 B2 | 4/2005 | Lipman | |
| 6,887,277 B2 | 5/2005 | Rauscher et al. | |
| 6,890,358 B2 | 5/2005 | Ball et al. | |
| 6,902,584 B2 | 6/2005 | Kwan et al. | |
| 6,942,699 B2 | 9/2005 | Stone et al. | |
| 6,953,478 B2 | 10/2005 | Bouttens et al. | |
| 6,969,406 B2 | 11/2005 | Tornier | |
| 7,011,686 B2 | 3/2006 | Ball et al. | |
| 7,033,396 B2 | 4/2006 | Tornier | |
| 7,044,973 B2 | 5/2006 | Rockwood, Jr. et al. | |
| 7,051,417 B2 | 5/2006 | Michelson | |
| 7,066,959 B2 | 6/2006 | Errico et al. | |
| 7,097,663 B1 | 8/2006 | Nicol et al. | |
| 7,108,719 B2 | 9/2006 | Horber | |
| 7,160,328 B2 | 1/2007 | Rockwood, Jr. et al. | |
| 7,166,132 B2 | 1/2007 | Callaway et al. | |
| 7,169,184 B2 | 1/2007 | Dalla Pria | |
| 7,175,663 B1 | 2/2007 | Stone | |
| 7,189,261 B2 | 3/2007 | Dews et al. | |
| 7,195,645 B2 | 3/2007 | Disilvestro et al. | |
| 7,238,207 B2 | 7/2007 | Blatter et al. | |
| 7,238,208 B2 | 7/2007 | Camino et al. | |
| 7,250,550 B2 | 7/2007 | Overby et al. | |
| 7,297,163 B2 | 11/2007 | Huebner | |
| 7,309,360 B2 | 12/2007 | Tornier et al. | |
| 7,329,284 B2 | 2/2008 | Maroney et al. | |
| 7,338,498 B2 | 3/2008 | Long et al. | |
| 7,338,528 B2 | 3/2008 | Stone et al. | |
| 7,344,565 B2 | 3/2008 | Seyer et al. | |
| 7,462,197 B2 | 12/2008 | Tornier et al. | |
| 7,465,319 B2 | 12/2008 | Tornier | |
| 7,476,253 B1 | 1/2009 | Craig et al. | |
| 7,520,898 B2 | 4/2009 | Re et al. | |
| 7,585,327 B2 | 9/2009 | Winslow | |
| 7,604,637 B2 | 10/2009 | Johnson et al. | |
| 7,615,080 B2 | 11/2009 | Ondrla | |
| 7,648,530 B2 | 1/2010 | Habermeyer et al. | |
| 7,670,382 B2 | 3/2010 | Parrott et al. | |
| 7,678,150 B2 | 3/2010 | Tornier et al. | |
| 7,758,650 B2 | 7/2010 | Dews et al. | |
| 7,887,544 B2 | 2/2011 | Tornier et al. | |

(56) References Cited

U.S. PATENT DOCUMENTS

| | | |
|---|---|---|
| D643,926 S | 8/2011 | Collins |
| 8,021,370 B2 | 9/2011 | Fenton et al. |
| 8,062,376 B2 | 11/2011 | Shultz et al. |
| 8,114,089 B2 | 2/2012 | Divoux et al. |
| 8,162,947 B2 | 4/2012 | Dreyfuss |
| 8,182,541 B2 | 5/2012 | Long et al. |
| 8,187,282 B2 | 5/2012 | Tornier et al. |
| 8,192,497 B2 | 6/2012 | Ondrla |
| 8,202,275 B2 | 6/2012 | Wozencroft |
| 8,231,682 B2 | 7/2012 | LaFosse |
| 8,246,687 B2 | 8/2012 | Katrana et al. |
| 8,277,512 B2 | 10/2012 | Parrott et al. |
| 8,317,871 B2 | 11/2012 | Stone et al. |
| 8,366,713 B2 | 2/2013 | Long et al. |
| 8,409,798 B2 | 4/2013 | Luy et al. |
| 8,414,586 B2 | 4/2013 | Cawthan et al. |
| 8,419,798 B2 | 4/2013 | Ondrla et al. |
| D685,474 S | 7/2013 | Courtney |
| 8,500,744 B2 | 8/2013 | Wozencroft et al. |
| 8,506,638 B2 | 8/2013 | Vanasse et al. |
| 8,512,410 B2 | 8/2013 | Metcalfe et al. |
| 8,591,592 B2 | 11/2013 | Dreyfuss |
| 8,690,958 B2 | 4/2014 | Klawitter et al. |
| 8,702,800 B2 | 4/2014 | Linares et al. |
| 8,753,402 B2 | 6/2014 | Winslow et al. |
| 8,840,671 B2 | 9/2014 | Ambacher |
| 8,845,742 B2 | 9/2014 | Kusogullari et al. |
| 8,864,834 B2 | 10/2014 | Boileau et al. |
| 8,870,962 B2 | 10/2014 | Roche et al. |
| 8,876,908 B2 | 11/2014 | Katrana et al. |
| 8,882,845 B2 | 11/2014 | Wirth et al. |
| 8,974,536 B2 | 3/2015 | Walch et al. |
| 9,089,435 B2 | 7/2015 | Walch et al. |
| D745,678 S | 12/2015 | Courtney et al. |
| 9,233,003 B2 | 1/2016 | Roche et al. |
| 9,326,865 B2 | 5/2016 | Katrana et al. |
| 9,408,652 B2 | 8/2016 | Hassler et al. |
| 10,251,755 B2 | 4/2019 | Boileau et al. |
| 10,413,416 B2 | 9/2019 | Boileau et al. |
| 10,695,195 B2 | 6/2020 | Hassler et al. |
| 2001/0032021 A1 | 10/2001 | McKinnon |
| 2001/0047210 A1 | 11/2001 | Wolf |
| 2001/0049561 A1 | 12/2001 | Dews et al. |
| 2002/0032484 A1 | 3/2002 | Hyde |
| 2002/0099381 A1 | 7/2002 | Maroney |
| 2002/0138148 A1 | 9/2002 | Hyde |
| 2002/0143402 A1 | 10/2002 | Steinberg |
| 2002/0151982 A1 | 10/2002 | Masini |
| 2002/0156534 A1 | 10/2002 | Grusin et al. |
| 2002/0177901 A1 | 11/2002 | Howie |
| 2003/0009171 A1 | 1/2003 | Tornier |
| 2003/0028253 A1 | 2/2003 | Stone et al. |
| 2003/0065397 A1 | 4/2003 | Hanssen et al. |
| 2003/0097183 A1 | 5/2003 | Rauscher et al. |
| 2003/0114933 A1 | 6/2003 | Bouttens et al. |
| 2003/0125809 A1 | 7/2003 | Iannotti et al. |
| 2003/0125810 A1 | 7/2003 | Sullivan et al. |
| 2003/0149485 A1 | 8/2003 | Tornier |
| 2003/0158605 A1 | 8/2003 | Tornier |
| 2003/0181916 A1 | 9/2003 | Wolford |
| 2004/0002765 A1 | 1/2004 | Maroney et al. |
| 2004/0006392 A1 | 1/2004 | Grusin et al. |
| 2004/0030394 A1 | 2/2004 | Horber |
| 2004/0034431 A1 | 2/2004 | Maroney et al. |
| 2004/0064189 A1 | 4/2004 | Maroney et al. |
| 2004/0064190 A1 | 4/2004 | Ball et al. |
| 2004/0068320 A1 | 4/2004 | Robie et al. |
| 2004/0133276 A1 | 7/2004 | Lang et al. |
| 2004/0138754 A1 | 7/2004 | Lang et al. |
| 2004/0148033 A1 | 7/2004 | Schroeder |
| 2004/0193168 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0210317 A1 | 10/2004 | Maroney et al. |
| 2004/0220673 A1 | 11/2004 | Pria |
| 2004/0220674 A1 | 11/2004 | Pria |
| 2004/0225367 A1 | 11/2004 | Glien et al. |
| 2004/0230197 A1 | 11/2004 | Tornier et al. |
| 2004/0249383 A1 | 12/2004 | White et al. |
| 2004/0267370 A1 | 12/2004 | Ondrla |
| 2005/0008672 A1 | 1/2005 | Winterbottom et al. |
| 2005/0010304 A1 | 1/2005 | Jamali |
| 2005/0015154 A1 | 1/2005 | Lindsey et al. |
| 2005/0033443 A1* | 2/2005 | Blatter .................. A61F 2/4014 623/19.14 |
| 2005/0043805 A1 | 2/2005 | Chudik |
| 2005/0049709 A1 | 3/2005 | Tornier |
| 2005/0060039 A1 | 3/2005 | Cyprien |
| 2005/0065612 A1 | 3/2005 | Winslow |
| 2005/0085919 A1 | 4/2005 | Durand-Allen et al. |
| 2005/0085921 A1 | 4/2005 | Gupta et al. |
| 2005/0090902 A1 | 4/2005 | Masini |
| 2005/0107882 A1* | 5/2005 | Stone .................. A61B 17/1684 623/19.14 |
| 2005/0113837 A1 | 5/2005 | Salyer |
| 2005/0113931 A1 | 5/2005 | Horber |
| 2005/0119531 A1 | 6/2005 | Sharratt |
| 2005/0143818 A1 | 6/2005 | Yuan et al. |
| 2005/0143829 A1 | 6/2005 | Ondrla et al. |
| 2005/0159751 A1 | 7/2005 | Berthusen et al. |
| 2005/0165490 A1 | 7/2005 | Tornier |
| 2005/0177241 A1 | 8/2005 | Angibaud et al. |
| 2005/0186247 A1* | 8/2005 | Hunter .................. A61B 17/11 424/423 |
| 2005/0197708 A1 | 9/2005 | Stone et al. |
| 2005/0209700 A1 | 9/2005 | Rockwood et al. |
| 2005/0216092 A1 | 9/2005 | Marik et al. |
| 2005/0240267 A1 | 10/2005 | Randall et al. |
| 2005/0245934 A1 | 11/2005 | Tuke et al. |
| 2005/0251263 A1 | 11/2005 | Forrer et al. |
| 2005/0256584 A1 | 11/2005 | Farrar |
| 2005/0261775 A1 | 11/2005 | Baum et al. |
| 2005/0267590 A1 | 12/2005 | Lee |
| 2005/0278030 A1 | 12/2005 | Tornier et al. |
| 2005/0278031 A1 | 12/2005 | Tornier et al. |
| 2005/0278032 A1 | 12/2005 | Tornier et al. |
| 2005/0278033 A1 | 12/2005 | Tornier et al. |
| 2005/0288681 A1 | 12/2005 | Klotz et al. |
| 2005/0288791 A1 | 12/2005 | Tornier et al. |
| 2006/0004462 A1 | 1/2006 | Gupta |
| 2006/0009852 A1 | 1/2006 | Winslow et al. |
| 2006/0020344 A1 | 1/2006 | Shultz et al. |
| 2006/0025796 A1 | 2/2006 | Merced-O'Neill |
| 2006/0030946 A1 | 2/2006 | Ball et al. |
| 2006/0111787 A1 | 5/2006 | Bailie et al. |
| 2006/0122705 A1 | 6/2006 | Morgan |
| 2006/0195110 A1 | 8/2006 | White et al. |
| 2006/0200249 A1 | 9/2006 | Beguin et al. |
| 2006/0235539 A1 | 10/2006 | Blunn et al. |
| 2006/0241775 A1 | 10/2006 | Buss |
| 2007/0078516 A1 | 4/2007 | Emami |
| 2007/0142916 A1 | 6/2007 | Olson, Jr. et al. |
| 2007/0156246 A1 | 7/2007 | Meswania et al. |
| 2007/0156250 A1 | 7/2007 | Seitz et al. |
| 2007/0162141 A1 | 7/2007 | Dews et al. |
| 2007/0173945 A1* | 7/2007 | Wiley .................. A61F 2/30734 623/19.13 |
| 2007/0179562 A1* | 8/2007 | Nycz .................. A61N 1/205 607/51 |
| 2007/0198087 A1 | 8/2007 | Coleman et al. |
| 2007/0225817 A1 | 9/2007 | Reubelt et al. |
| 2007/0225818 A1 | 9/2007 | Reubelt et al. |
| 2007/0225821 A1 | 9/2007 | Reubelt et al. |
| 2007/0244564 A1 | 10/2007 | Ferrand et al. |
| 2007/0250174 A1 | 10/2007 | Tornier et al. |
| 2007/0276509 A1 | 11/2007 | Ratcliffe et al. |
| 2008/0021564 A1 | 1/2008 | Gunther |
| 2008/0183297 A1 | 7/2008 | Boileau et al. |
| 2009/0125113 A1 | 5/2009 | Guederian et al. |
| 2009/0171462 A1 | 7/2009 | Poncet et al. |
| 2009/0270993 A1 | 10/2009 | Maisonneuve et al. |
| 2009/0287309 A1 | 11/2009 | Walch et al. |
| 2009/0292364 A1 | 11/2009 | Linares |

(56) References Cited

U.S. PATENT DOCUMENTS

| | | | |
|---|---|---|---|
| 2009/0306782 A1 | 12/2009 | Schwyzer | |
| 2010/0087927 A1 | 4/2010 | Roche et al. | |
| 2010/0114326 A1 | 5/2010 | Winslow et al. | |
| 2010/0191340 A1 | 7/2010 | Dreyfuss | |
| 2010/0274360 A1 | 10/2010 | Gunther | |
| 2010/0280517 A1 | 11/2010 | Cawthan et al. | |
| 2010/0280518 A1 | 11/2010 | Gary | |
| 2011/0098822 A1 | 4/2011 | Walch et al. | |
| 2011/0166661 A1 | 7/2011 | Boileau et al. | |
| 2011/0213372 A1 | 9/2011 | Keefer et al. | |
| 2011/0224673 A1 | 9/2011 | Smith | |
| 2011/0264153 A1 | 10/2011 | Hassler et al. | |
| 2011/0276144 A1 | 11/2011 | Wirth et al. | |
| 2011/0313533 A1 | 12/2011 | Gunther | |
| 2012/0109321 A1 | 5/2012 | Stone et al. | |
| 2012/0265315 A1 | 10/2012 | Kusogullari et al. | |
| 2012/0296435 A1 | 11/2012 | Ambacher | |
| 2013/0123930 A1 | 5/2013 | Burt | |
| 2013/0173006 A1 | 7/2013 | Duport | |
| 2013/0178943 A1 | 7/2013 | Duport | |
| 2013/0190882 A1 | 7/2013 | Humphrey | |
| 2013/0211539 A1 | 8/2013 | McDaniel et al. | |
| 2013/0261626 A1 | 10/2013 | Chavarria et al. | |
| 2013/0261629 A1 | 10/2013 | Anthony et al. | |
| 2013/0261754 A1 | 10/2013 | Anthony et al. | |
| 2014/0058523 A1 | 2/2014 | Walch et al. | |
| 2014/0107792 A1 | 4/2014 | Hopkins et al. | |
| 2014/0156012 A1 | 6/2014 | Winslow | |
| 2014/0296988 A1 | 10/2014 | Winslow et al. | |
| 2014/0358239 A1 | 12/2014 | Katrana et al. | |
| 2014/0358240 A1 | 12/2014 | Katrana et al. | |
| 2015/0012104 A1 | 1/2015 | Boileau et al. | |
| 2016/0324648 A1 | 11/2016 | Hodorek et al. | |
| 2016/0331555 A1 | 11/2016 | Hassler et al. | |
| 2017/0042687 A1 | 2/2017 | Boileau et al. | |
| 2019/0358045 A1 | 11/2019 | Boileau et al. | |

FOREIGN PATENT DOCUMENTS

| | | | |
|---|---|---|---|
| DE | 4220217 | 12/1993 | |
| DE | 19509037 | 9/1996 | |
| DE | 19630298 | 1/1998 | |
| DE | 10233204 | 1/2004 | |
| DE | 102004042502 | 3/2006 | |
| EP | 0 274 094 | 8/1990 | |
| EP | 0257359 | 11/1991 | |
| EP | 0299889 | 3/1992 | |
| EP | 0524857 | 1/1993 | |
| EP | 0529480 | 6/1993 | |
| EP | 0617934 | 10/1994 | |
| EP | 0679375 | 11/1995 | |
| EP | 0712617 | 5/1996 | |
| EP | 0715836 | 6/1996 | |
| EP | 0599429 | 10/1997 | |
| EP | 0797964 | 10/1997 | |
| EP | 0864306 | 9/1998 | |
| EP | 0903128 | 3/1999 | |
| EP | 1062923 | 12/2000 | |
| EP | 0664108 | 8/2002 | |
| EP | 0809986 | 10/2002 | |
| EP | 0927548 | 5/2003 | |
| EP | 1323395 | 7/2003 | |
| EP | 0807426 | 10/2003 | |
| EP | 1380274 | 1/2004 | |
| EP | 1402853 | 3/2004 | |
| EP | 1 413 265 | 4/2004 | |
| EP | 0 959 822 | 5/2004 | |
| EP | 1477120 | 11/2004 | |
| EP | 1 125 565 | 12/2004 | |
| EP | 1 518 519 | 3/2005 | |
| EP | 1 004 283 | 5/2005 | |
| EP | 1195149 | 7/2005 | |
| EP | 1064890 | 9/2005 | |
| EP | 1570816 | 9/2005 | |
| EP | 1607069 | 12/2005 | |
| EP | 1 652 482 | 5/2006 | |
| EP | 1 762 191 | 3/2007 | |
| EP | 0903127 | 6/2007 | |
| EP | 1952788 | 1/2008 | |
| EP | 1952771 | 8/2008 | |
| EP | 1952788 | 8/2008 | |
| EP | 1402854 | 7/2010 | |
| EP | 1 867 303 | 9/2010 | |
| EP | 1 977 720 | 1/2011 | |
| EP | 1 550 420 | 2/2012 | |
| EP | 2 261 303 | 11/2012 | |
| EP | 1 706 074 | 12/2012 | |
| EP | 2 564 814 | 3/2013 | |
| EP | 2 567 676 | 3/2013 | |
| EP | 2 574 313 | 4/2013 | |
| EP | 2 616 013 | 7/2013 | |
| EP | 2 474 288 | 9/2013 | |
| EP | 2 663 263 | 5/2014 | |
| EP | 2 502 605 | 8/2014 | |
| EP | 2 800 541 | 11/2014 | |
| EP | 2 815 726 | 8/2015 | |
| EP | 2 353 549 | 6/2016 | |
| EP | 1952771 | 10/2016 | |
| EP | 3335676 | 6/2018 | |
| FR | 2216981 | 9/1974 | |
| FR | 2248820 | 5/1975 | |
| FR | 2545352 | 11/1984 | |
| FR | 2574283 | 6/1986 | |
| FR | 2652498 | 4/1991 | |
| FR | 2664809 | 1/1992 | |
| FR | 2 674 122 | 9/1992 | |
| FR | 2699400 | 6/1994 | |
| FR | 2704747 | 11/1994 | |
| FR | 2721200 | 12/1995 | |
| FR | 2726994 | 5/1996 | |
| FR | 2737107 | 1/1997 | |
| FR | 2835425 | 8/2003 | |
| FR | 2836039 | 8/2003 | |
| SU | 749392 | 7/1980 | |
| WO | WO 1991/007932 | 6/1991 | |
| WO | WO 1993/009733 | 5/1993 | |
| WO | WO 1996/017553 | 6/1996 | |
| WO | WO 1998/046172 | 10/1998 | |
| WO | WO 1999/049792 | 10/1999 | |
| WO | WO 1999/065413 | 12/1999 | |
| WO | WO 2000/015154 | 3/2000 | |
| WO | WO 2000/041653 | 7/2000 | |
| WO | WO 2000/062718 | 10/2000 | |
| WO | WO 2001/047442 | 7/2001 | |
| WO | WO 01/67988 | 9/2001 | |
| WO | WO 02/17822 | 3/2002 | |
| WO | WO 2002/039931 | 5/2002 | |
| WO | WO 2002/039933 | 5/2002 | |
| WO | WO 2002/049516 | 6/2002 | |
| WO | WO 2002/067821 | 9/2002 | |
| WO | WO 2003/005933 | 1/2003 | |
| WO | WO 2003/092513 | 11/2003 | |
| WO | WO 2003/094806 | 11/2003 | |
| WO | WO 2006/039483 | 4/2006 | |
| WO | WO 2007/109340 | 9/2007 | |
| WO | WO 2008/011078 | 1/2008 | |
| WO | WO-2008015724 A2 * | 2/2008 | ............... A61F 2/40 |
| WO | WO 2007/109291 | 4/2008 | |
| WO | WO 2007/109319 | 6/2008 | |
| WO | WO 2008/146124 | 12/2008 | |
| WO | WO 2011/081797 | 7/2011 | |
| WO | WO 2012/035263 | 3/2012 | |
| WO | WO 2012/130524 | 10/2012 | |
| WO | WO 2013/009407 | 1/2013 | |
| WO | WO 2013/064569 | 5/2013 | |
| WO | WO 2013/148229 | 10/2013 | |
| WO | WO 2014/005644 | 1/2014 | |
| WO | WO 2014/058314 | 4/2014 | |
| WO | WO 2015/112307 | 7/2015 | |

OTHER PUBLICATIONS

(56) References Cited

OTHER PUBLICATIONS

"Aequalis®—Glenold Keeled and Pegged—Surgical Technique," Tornier, Inc., 12 pp.
"Anatomic Glenoid, Surgical Technique," Smith & Nephew, 2000, 6 pp.
"Anatomical Shoulder1M System—The new removable head option," Zimmer Inc., 2004, 6 pp.
"Bigliani/FlatoW®—The Complete Shoulder Solution, Designed by Shoulder Surgeons for Shoulder Surgery," Zimmer, Inc., 2001, 6 pp.
"Delta CT A 1M Reverse Shoulder Prosthesis," DePuy International, Ltd., 2004, 28 pp.
"Offset Head, Bio-Modular® Total Shoulder," Biomet, Inc. 2000, 2 pp.
"The Foundation® Total Shoulder System," Encore Surgical, 2 pp.
"The Townley Modular Shoulder, Design by Reason," Biopro, Inc., 2 pp.
"Tornier Surgical Technique Addendum, Tornier Aequalis® Reversed Hemi-Adaptor Technique," Tornier, Inc., Aug. 8, 2005, 1 pg.
"Zimmer® Shoulder Retractors," Zimmer, Inc., 2000, 2 pp.
"Aequalis® Press-Fit Shoulder Prosthesis—Surgical Technique," Tornier, Inc.
"Aequalis—Fracture Shoulder Prosthesis—Surgical Technique," Tornier, Inc.
"Aequalis—Fracture Suture Technique in 5 Steps," Tornier, Inc.
"Anatomical Shoulder™—Cemented Shoulder Prosthesis Product Information and Surgical Technique," Sulzer Medica, 2000.
"Anatomical Shoulder™ System Surgical Technique—Removable head option for improved surgical results," Zimmer, Inc., 2004.
"Bio-Modular Total Shoulder Surgical Technique," Biomet Orthopedics, Inc., 2001.
"Bio-Modular® / Bi-Polar Shoulder Arthroplasty," Biomet, Inc., 1997.
"Bio-Modular® Choice, Shoulder System," Biomet Orthopedics, Inc., 2004.
"Copeland™ Humeral Resurfacing Head," Biomet Orthopedics, Inc., 2001.
"Design Rationale," Latitude®.
"Global C.A.P.™ Surgical technique, resurfacing humeral head implant," DePuy International, Ltd., 2004.
Apoil, Andrew "A Condyle for the Rotator Cuff Muscles, the total shoulder prosthesis," Aesculap®, 1994, 4 pp.
Beuchel M.D., Frederick F. "Beuchel-Pappas™ Modular Salvage Shoulder System," Endotec, Inc., 2000, 8 pp.
Beuchel M.D., Frederick F. "Beuchel-Pappas™ Resurfacing Shoulder System," Endotec, Inc., 2009, 9 pp.
Beuchel M.D., Frederick F. "Beuchel-Pappas™ Total Shoulder System," Endotec, Inc., 2000, 16 pp.
Bigliani/Flatow®—The Complete Shoulder Solution, 4-Part Fracture of the Humerus Surgical Technique, Zimmer, Inc., 2000.
Boileau, et al. "Adaptability and modularity of shoulder prosthese, "Maitrise Orthopédique, https://www.maitriseorthop.com/corpusmaitri/orthopaedic/prothese_epaule_orthop/boileau_us.shtml, Jan. 3, 2006.
Boileau, et al. "Arthoscopic Repair of Full-Thickness Tears of the Supraspinatus: Does the tendon really heal?," The Journal of Bone and Joint Surgery, Inc., pp. 1229-1240, 2005.
Cofield, M.D., Robert H. "Cofield2 Total Shoulder System, Surgical Technique," Smith & Nephew, 1997, 32 pp.
Hertel M.D., PO, Ralph, "Technical considerations for implantation of EPOCA glenoid components (Leseprobe)," Epoca Newsletter, May 14, 2001, 1 pg.
John M. Fenlin Jr., M.D., Symposium on Surgery of the Shoulder, "Total Glenohumeral Joint Replacement," Orthopedic Clinics of North America, vol. 6, No. 2, Apr. 1975, pp. 565-583.
Klein, Travis J., et al, "Mechanically favorable bone remodeling in rotator cuff arthropathy patients with good function," Minneapolis Sports Medicine Center and University of Minnesota, 2 pp.
Mansat, Michel, "Neer 31M, Surgical Technique for Fractures" Smith & Nephew, 2000, 19 pp.
Mole, M.D., et al., "Aequalis-Reversed™ Shoulder Prosthesis, Surgical Technique," Tornier, Inc., 24 pp.
Nicholson, Gregory P., "Arthroplasty and Rotator Cuff Deficiency," Chapter 7, pp. 149-166.
Zimmer® BiglianiFlatoW®—The Complete Shoulder Solution, Total Shoulder Arthroplasty Surgical Technique, Zimmer, Inc., 2003, pp. 1-30.
"Tornier Aequalis® Reversed 2 Prong Capsular Retractor," Tornier, Inc., Oct. 8, 2005.
"Tornier Aequalis® Reversed Shoulder G2 Baseplate," Tornier, Inc., Oct. 8, 2005.
Search Report for European Appl. No. 08356017.7 dated Jun. 4, 2008 in 5 pages.
Search Report for European Appl. No. 08356018.5 dated Jun. 16, 2008 in 6 pages.
Office Communication for European Appl. No. 08356017.7 dated May 26, 2015 in 6 pages.
Office Communication for European Appl. No. 08356018.5 dated Mar. 16, 2015 in 5 pages.
Office Communication for European Appl. No. 08356018.5 dated Dec. 1, 2015 in 3 pages.
"Aequalis Resurfacing Head", retrieved from http://www/tornier-us.com/upper/shoulder/shorec004/index.php?pop+1 on Apr. 14, 2010.

* cited by examiner

INTRA-ARTICULAR JOINT REPLACEMENT

CROSS REFERENCE TO RELATED APPLICATIONS

The present application is a continuation of U.S. patent application Ser. No. 14/069,158, entitled Intra-Articular Joint Replacement, filed Oct. 31, 2013, which is a continuation of U.S. patent application Ser. No. 12/787,124, entitled Intra-Articular Joint Replacement, filed May 25, 2010, which is a continuation of U.S. patent application Ser. No. 12/337,385, entitled Intra-Articular Joint Replacement, filed Dec. 17, 2008, which is a continuation-in-part of U.S. patent application Ser. No. 12/020,913, entitled Method and Apparatus for Fitting a Shoulder Prosthesis, filed Jan. 28, 2008, which claims priority to French application No. 0700622, entitled "Méthode et ensemble d'instrumentation chirurgicale pour poser une prothèse totale d'épaule inversée, et prothèse correspondante," filed Jan. 30, 2007, and also claims the benefit of U.S. Provisional Application Ser. Nos. 60/888,437 filed Feb. 6, 2007 and 60/971,762 filed Sep. 12, 2007, both entitled "Method and Apparatus for Fitting an Inverted Shoulder Prosthesis," and U.S. Provisional Application Ser. No. 61/015,042, entitled "Intra-Articular Joint Replacement," filed Dec. 19, 2007, the complete disclosures of which are hereby incorporated by reference.

TECHNICAL FIELD

The present invention relates to a method and apparatus for implanting a prosthesis at the intersection of two or more bone, and in particular, to a method and apparatus for processing and implanting a resected portion of a humerus to act as an articular surface for an interpositional implant of a shoulder prosthesis.

BACKGROUND OF THE INVENTION

In the field of total shoulder prostheses, prostheses are commonly said to be inverted when they comprise a glenoid component that is integral with the glenoid surface of a scapula of a patient's shoulder and that delimits a convex articular surface and a humeral component that is integral with the humerus of the patient's shoulder and that delimits a concave articular surface. The cooperation of the articular surfaces of the glenoid and humeral components allow an articulated connection to be reproduced at the shoulder. However, it is common with this type of prosthesis that during adductive movement of the shoulder, the lower portion of the humeral prosthetic component strikes the pillar of the scapula, i.e. the lower portion of the glenoid located just below the glenoid prosthetic component (when the patient is standing upright). This interference between the humeral prosthetic component and the scapula limits the range of adductive movement of the shoulder and may cause pain to the patient or even lead to the prosthesis becoming dislodged due to, for example, osteolysis of the scapula.

Another method used to replace damaged shoulder joints is interpositional arthroplasty. The method of interpositional arthroplasty uses tissue from the patient or an artificial replacement to repair a damaged or malformed joint. An interpositional implant is positioned at the joint to act as an engagement surface between two adjacent bone structures to allow articular movement. In the particular field of interpositional shoulder arthroplasty, the humeral metaphysis is typically impacted to form an engagement surface for an interpositional implant positioned between a glenoid component (or glenoid) and a humeral component (or humeral metaphysis). However, if the cancellous bone in the humeral metaphysis is of poor or degraded quality, the cancellous bone may lead to gradual subsidence of the interpositional implant within the humeral metaphysis. It is thus desirable to develop an interpositional implant with a metaphyseal articular surface that will provide support and protection to the metaphyseal cancellous bone.

SUMMARY OF THE INVENTION

Some embodiments relate to a method of forming a shoulder prosthesis, including forming a concave articular surface into an end portion of a humerus, including compacting bone of the end portion to define the concave articular surface. An implant having a convex articular surface is secured to a glenoid. The concave articular surface of the humerus is articulated with the convex articular surface of the implant.

Other embodiments relate to a method of forming a shoulder prosthesis, including resecting an end portion of a humerus to form a resected end of the humerus and a resected portion separated from the humerus, the resected portion having an outer convex surface and an inner surface. The inner surface of the resected portion is processed to comprise a concave articular surface. The outer convex surface of the resected portion is implanted in the resected end of the humerus. An implant having a convex articular surface is secured to a glenoid. The concave articular surface of the resected portion is articulated with the convex articular surface of the implant.

Still other embodiments relate to a method of forming a shoulder prosthesis, including forming a recess in an end portion of a humerus and disposing a reinforcing structure across at least a portion of the recess to form a concave articular surface of the humerus. The reinforcing structure is attached to the humerus. An implant having a convex articular surface is secured to a glenoid. The concave articular surface of the resected portion is articulated directly with the convex articular surface of the implant.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE INVENTION

Figure 1A:
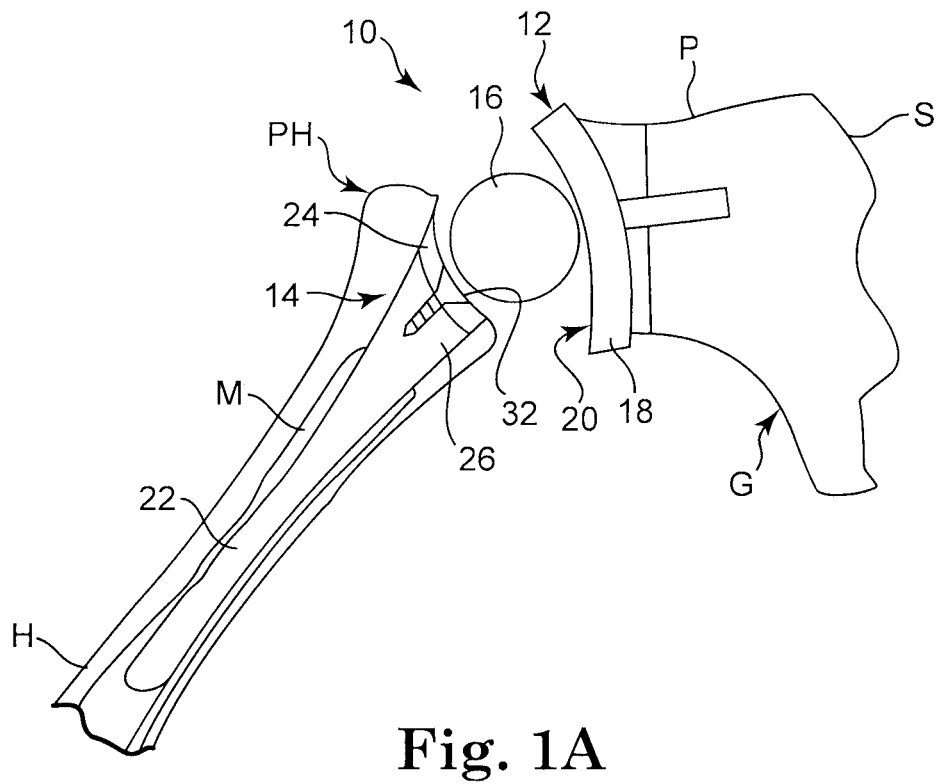
FIG. 1A is a schematic view of an intra-articular prosthesis implanted in a patient's shoulder in accordance with an embodiment of the present invention.

FIG. 1A shows a schematic view of a prosthesis 10 including a glenoid component 12, a humeral component 14 and an interpositional implant 16. The glenoid component 12 is implanted in the scapula S of the glenoid G. The method and apparatus of the various embodiments of the present invention disclosed herein may be used with a variety of glenoid components, such as for example those disclosed in U.S. Pat. Nos. 7,033,396; 6,953,478; 6,761,740; 6,626,946; 5,702,447 and U.S. Publication Nos. 2004/0220673; 2005/0278030; 2005/0278031; 2005/0278032; 2006/0020344, which are hereby incorporated by reference. Although the prosthesis 10 is primarily discussed as being implanted in a patient's shoulder, the prosthesis 10 may also be modified and implanted in other locations of a patient's body without departing from the intended scope of the present invention. For example, the prosthesis 10 may be modified to be implanted in a patient's hip, ankle, hands, or feet.

In the illustrated embodiment, the glenoid component 12 includes an articular member 18 with a generally concave articular surface 20 that engages the interpositional implant 16. Given that the articular member 18 is positioned immediately adjacent the glenoid G, the interpositional implant 16 is remote from the resected surface of the glenoid G in the sense that, if the articular member 18 were omitted, the interpositional implant 16 would be directly juxtaposed with the glenoid G. Thus, on account of the articular member 18, the interpositional implant 16 and the humeral component 14 are laterally remote from the glenoid G, limiting the risk of the humerus H interfering with the bottom of the glenoid G, i.e. with the pillar P of the scapula S. Alternatively, an articular member 18 may not be required within the glenoid G. In this case, the interpositional implant 16 would articulate directly with the glenoid G.

The humeral component 14 includes an articular member 24 formed from a resected portion 30 (shown in FIG. 3) of the proximal humerus PH that is removed during processing of the humerus H. The proximal humerus PH is preferably resected such that the resected portion 30 is preferably a single, unitary piece. In this form, an outer convex surface 58 of the resected portion 30 is implanted into the proximal humerus PH as a single unit, rather than as fragments.

Alternatively, the resected portion 30 can be formed from a single piece or a plurality of pieces taken from the proximal humerus PH or other locations in the patient's body. Implantation of the resected portion 30 can be supplemented with bone graft material, such as for example a purée of bone substance, bone replacements, bone fillers, bone cements and/or bone adhesives, or a combination thereof. The bone graft material can be formed from the patient's bone, an allograft, a xenograft, or a combination thereof. Various bone replacements, bone fillers, bone cements and bone adhesives are disclosed in U.S. Pat. No. 6,692,563 (Zimmerman), which is hereby incorporated by reference. Various additives can also be included with the resected portion, including, but not limited to bone growth agents and pain inhibitors.

As will be discussed further below, the resected portion 30 is prepared and impacted into the proximal humerus PH to form the articular member 24 having a concave articular surface 32. The preparation of the resected portion 30 can be performed ex vivo or in situ.

In the illustrated embodiment, the humeral component 14 includes an optional stem 22 located in the medullary cavity M of the humerus H. The proximal end 28 of the stem 22 supports the resected portion 30 and optionally serves as an attachment member. For example, a fastener 26 can optionally extend through the resected portion 30 and engage the stem 22. It will be appreciated that the stem 22 may be omitted entirely without departing from the intended scope of the present invention.

The interpositional implant 16 is positioned between the articular member 18 of the glenoid component 12 and the articular member 24 of the humeral component 14. The radius of the interpositional implant 16 is typically equal to or less than the radii of the concave surfaces 20 and 32 of the articular member 18 of the glenoid component 12 and the articular member 24 of the humeral component 14, respectively. When the interpositional implant 16 is positioned between the glenoid component 12 and the humeral component 14, as shown in FIG. 1A, the concave surfaces 20 and 32 are in mutual surface contact with the interpositional implant 16, allowing articular movements of the patient's shoulder.

Figure 1B:
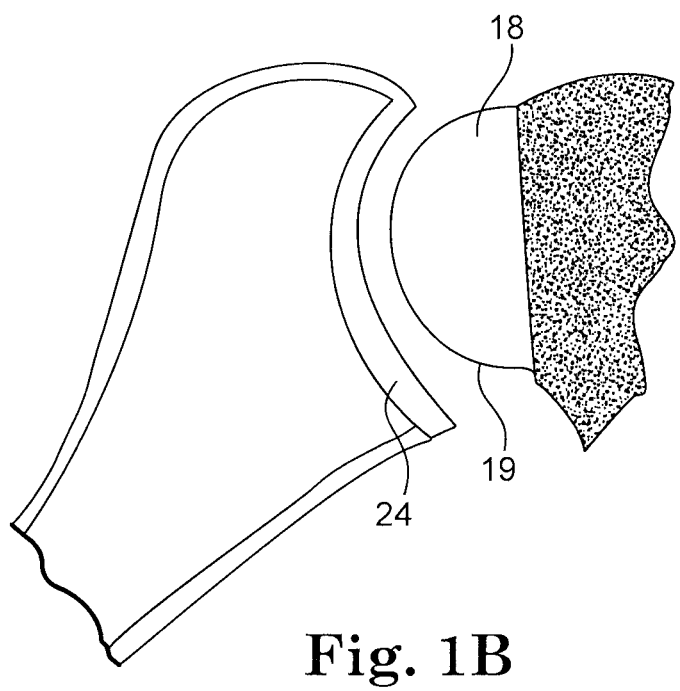
FIG. 1B is a schematic view of an alternate prosthesis implanted in a patient's shoulder in accordance with an embodiment of the present invention.

In an alternate embodiment illustrated in FIG. 1B, the interpositional implant 16 is eliminated and a glenoid component 18 with a convex articular surface 19 is substituted. The articular member 24, created as outlines in FIG. 1A, engages directly with the convex articular surface 19.

FIGS. 2-9 illustrate various embodiments for processing and implanting the prosthesis 10 into the humerus H. It is to be understood that the method of implanting the prosthesis 10 described hereinafter is merely a non-limiting illustrative example of a method and instruments used to implant the prosthesis 10. In other words, the method and the instruments specified hereinafter can be used to implant prostheses of a broad range of structures, of which, for example, the glenoid and/or humeral components 12, 14 consist of a plurality of metallic, plastic and/or ceramic-type parts joined together. As previously mentioned, the interpositional implant 16 may also articulate directly with the glenoid G such that the glenoid component 12 is not included as part of the prosthesis 10.

Figure 2:
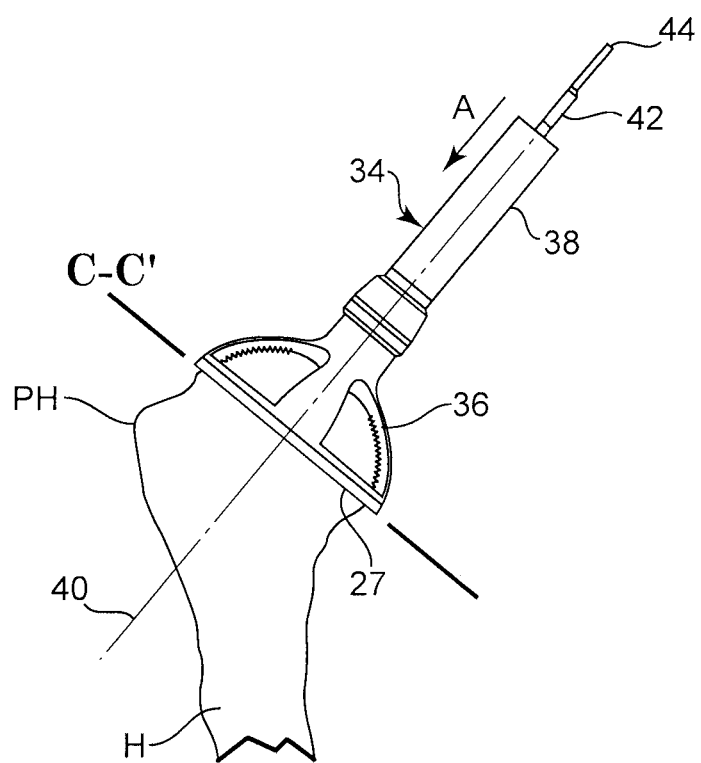
FIG. 2 is a schematic view of a cutting guide for a proximal portion of a humerus in accordance with an embodiment of the present invention.

FIG. 2 is a schematic view of a cutting guide 34 positioned over the proximal humerus PH. In order to prepare the proximal humerus PH for resection, the soft parts (i.e.

cartilage) of the proximal humerus PH may optionally be removed using a deltopectoral or supero-external approach.

The cutting guide 34 includes a bell-shaped body 36 secured to a shaft 38. An interior surface of the body 36 has a concave surface from which the main center of curvature pertains substantially to an axis 40 from which the shaft 38 extends from the body 36. The body 36 is designed to cover the upper portion of the proximal humerus PH in the manner of a cap and is perforated to give the surgeon a better view of the proximal humerus PH when positioning the body 36. The body 36 is thus shaped to reproduce approximately the surface features of the upper proximal humerus PH of a normal anatomical humerus H. However, in practice, there will be a range of a plurality of homothetic guiding instruments 34 having bodies 36 which have respective dimensions associated with the size and the state of the patient's bones.

The shaft 38 of the cutting guide 34 is optionally provided with a protruding tube 42 centered on the axis 40 and the main center of curvature of the body 36. Once the body 36 is properly positioned over the proximal humerus PH, a guide pin 44 having a pointed distal end is introduced into the protruding tube 42 and inserted into the proximal humerus PH. The guide pin 44 preferably terminates before the cutting plane C-C'. The surgeon uses the distal surface 27 on the body 36 located in the cutting plane C-C' to resect the portion 30 from the proximal humerus PH. Alternatively, the surgeon can cut free-hand without a template.

Figure 3:
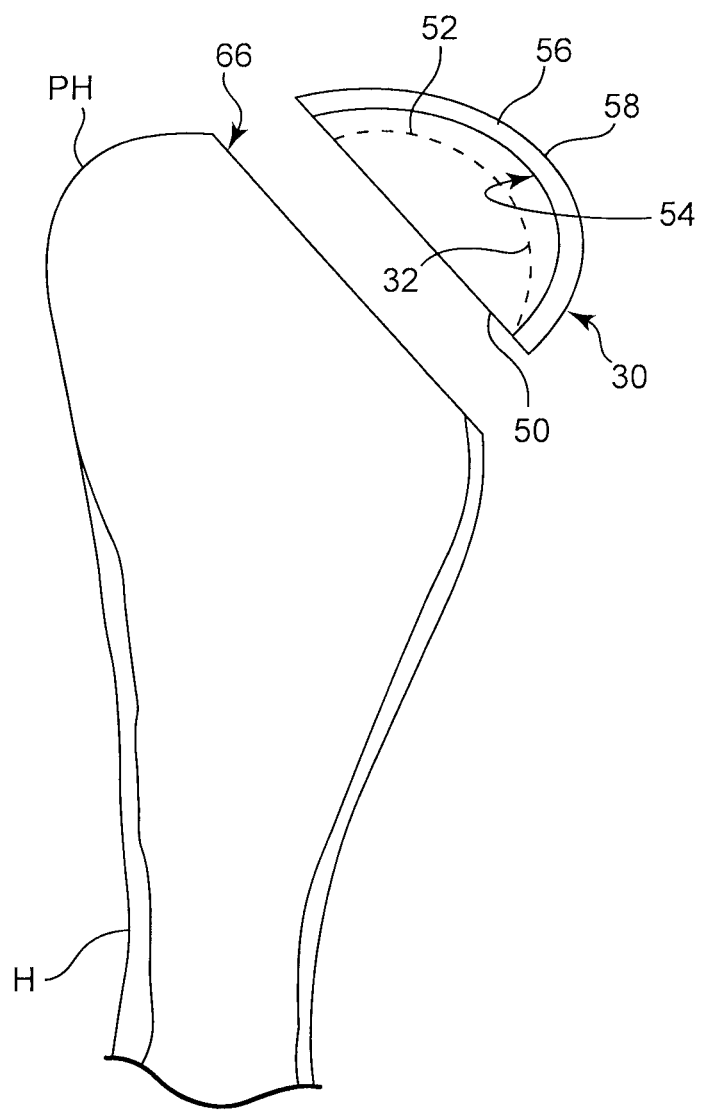
FIG. 3 is a schematic view of a resected portion of the proximal portion of the humerus in accordance with an embodiment of the present invention.

FIG. 3 shows a schematic view of the resected portion 30 of the proximal humerus PH. After the proximal humerus PH has been resected, the proximal humerus PH has a cut surface 66 where the resected portion 30 was removed. The resected portion 30 includes a convex outer surface 58 and an inner cut surface 50 of cancellous bone 52. In one embodiment, the resected portion 30 is prepared ex vivo by impacting the inner cut surface 50 to compress the cancellous bone 52 to form the inner concave surface 32. As a result, the inner concave surface 32 is a layer of compacted cancellous bone 52 pressed against the inner surface 54 of the cortical bone 56.

In another embodiment, the resected portion 30 is prepared ex vivo by removing the cancellous bone 52 from the cortical bone 56. As a result, the inner concave surface 32 is essentially the inner surface 54 of the cortical bone 56. Either of these procedures can also be performed in situ. That is, after the resected portion 30 is engaged with the proximal humerus PH.

Figure 4:
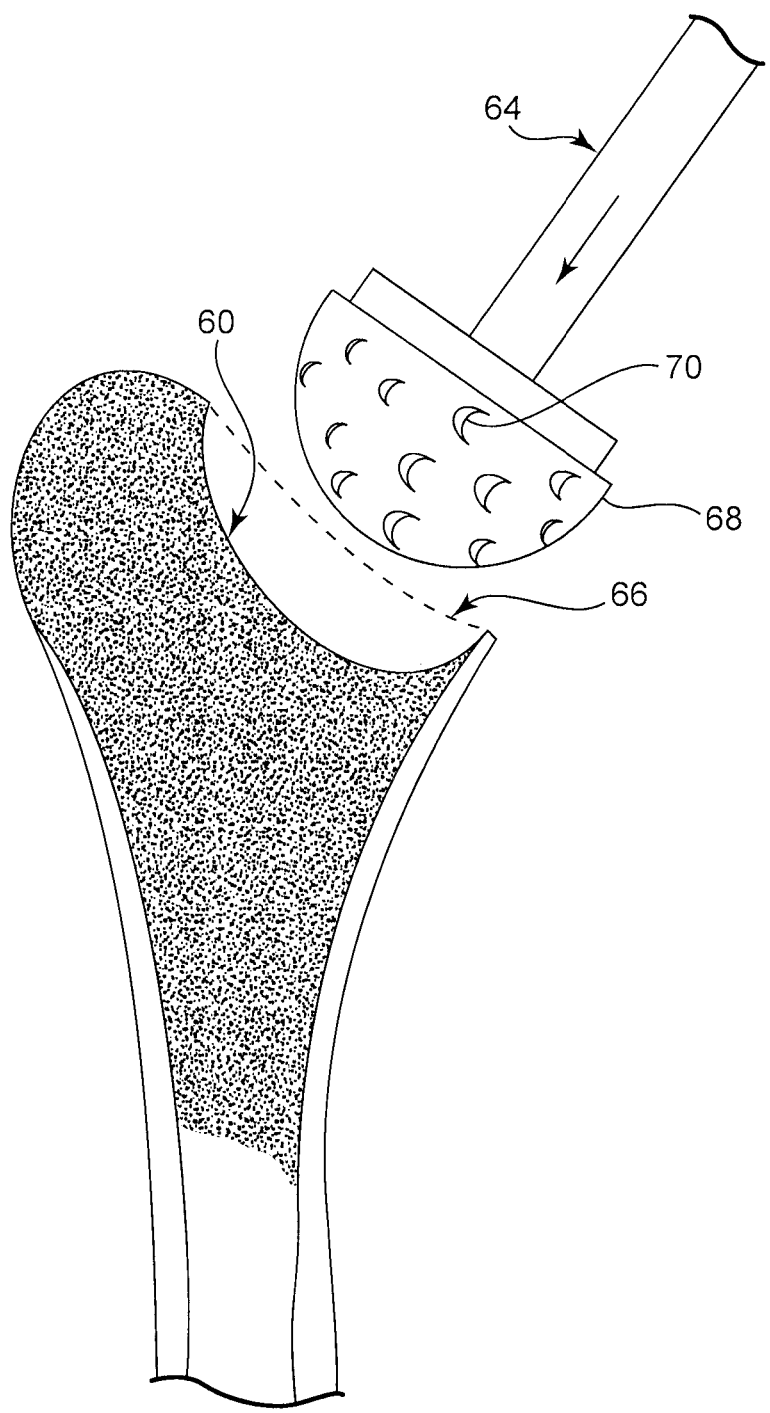
FIG. 4 is a schematic view of a method of preparing a resected proximal portion of the humerus in accordance with an embodiment of the present invention.

In some embodiments, the cut surface 66 of the proximal humerus PH is prepared to receive the resected portion 30. A hemispherical reaming instrument 64, shown in FIG. 4, is used to form a concave surface 60 in the proximal humerus PH. The reaming instrument 64 includes a convex body 68 having a plurality of teeth 70 to shape the cut surface 66 into the desired form. The concave surface 60 is preferably the same shape as the outer convex surface 58 of the resected portion 30.

In another embodiment, the cut surface 66 (shown in dashed lines) is compacted or carved to form the concave surface 60 on the proximal humerus PH. Preparing the cut surface 66 of the proximal humerus PH may be performed using a variety of other techniques known in the art without departing from the intended scope of the present invention. Small holes may optionally be drilled through the concave surface 60 to enhance bone integration remodeling once the resected portion 30 is reversed and implanted in the humerus H.

Figure 5:
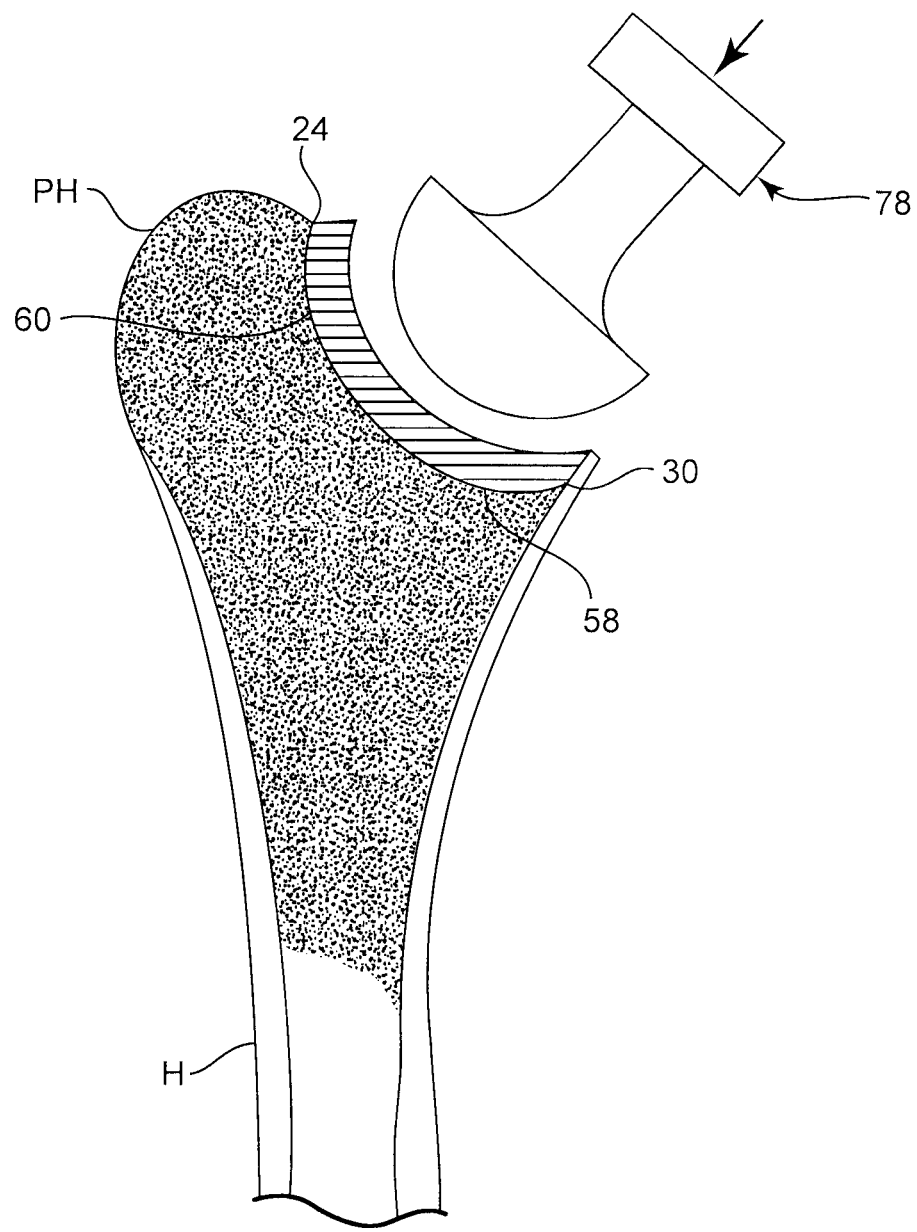
FIG. 5 is a schematic view of a method and apparatus for implanting the resected portion of the proximal portion of the humerus in accordance with an embodiment of the present invention.

FIG. 5 shows the resected portion 30 being impacted into engagement with the concave surface 60 of the proximal humerus PH. The resected portion 30 is positioned within the concave surface 60 such that the convex outer surface 58 engages the concave surface 60. An impacting instrument 78 is then used to drive the resected portion 30 into the proximal humerus PH to form the articular member 24 having a semi-spherical shape at the concave surface 60 of the proximal humerus PH. As the resected portion 30 is driven into the proximal humerus PH, cancellous bone at each side of the proximal humerus PH is compressed and forms to the shape of the concave surface 60.

Figure 6:
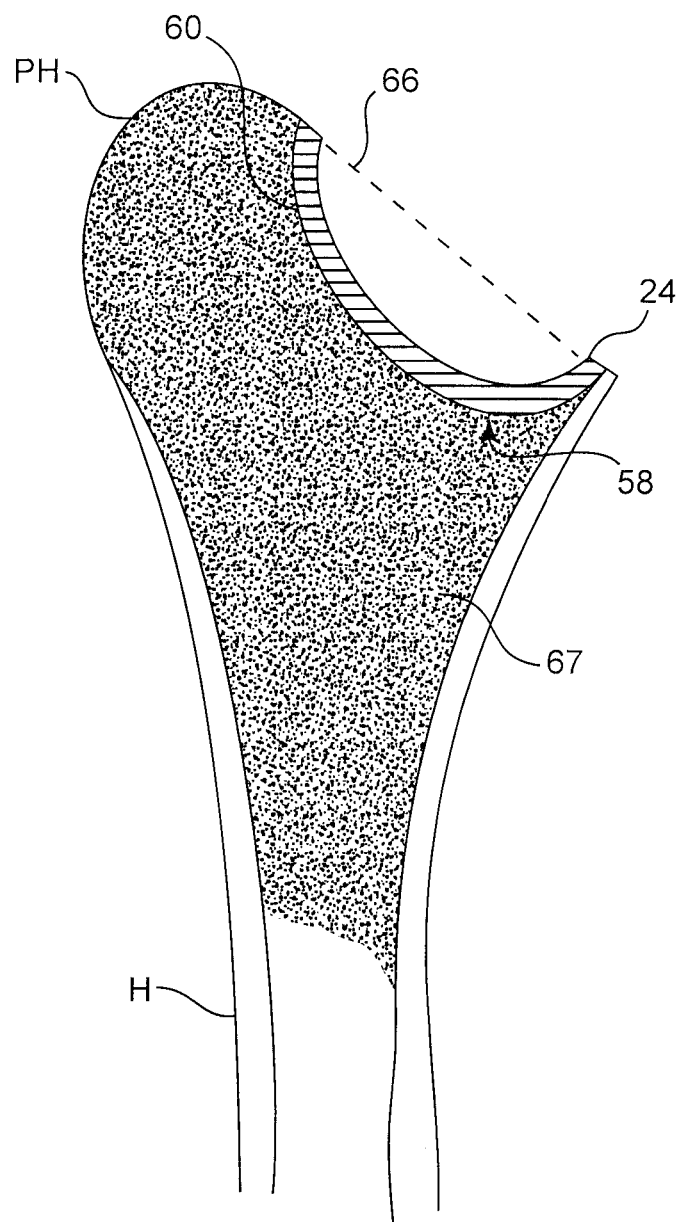
FIG. 6 is a schematic view of a resected portion implanted into a proximal portion of the humerus in accordance with an embodiment of the present invention.

In an alternate embodiment illustrated in FIG. 6, the resected portion 30 is compacted directly against the cut surface 66, without the reaming step shown in FIG. 4. By gradually integrating the resected portion 30 into the proximal humerus PH, a strong bony or fibrous-cartilaginous underlying support structure having the concave surface 60 is created to support the articular member 24. In addition, the resected portion 30 is used to isolate the cancellous bone 67 in the humerus H from synovial fluids. The resected portion 30 is preferably driven into the proximal humerus PH as a single unit such that the resulting articular member 24 is an integral piece and is not formed of fragmented pieces. The articular member 24 has a shape of a metaphyseal cup formed to cooperate with a variety of interpositional components, such as, for example, a full sphere, a lens-type free interpositional component, or a combination thereof. In one embodiment, the articular member 24 may have a shape of approximately one-third of a sphere.

Figure 7:
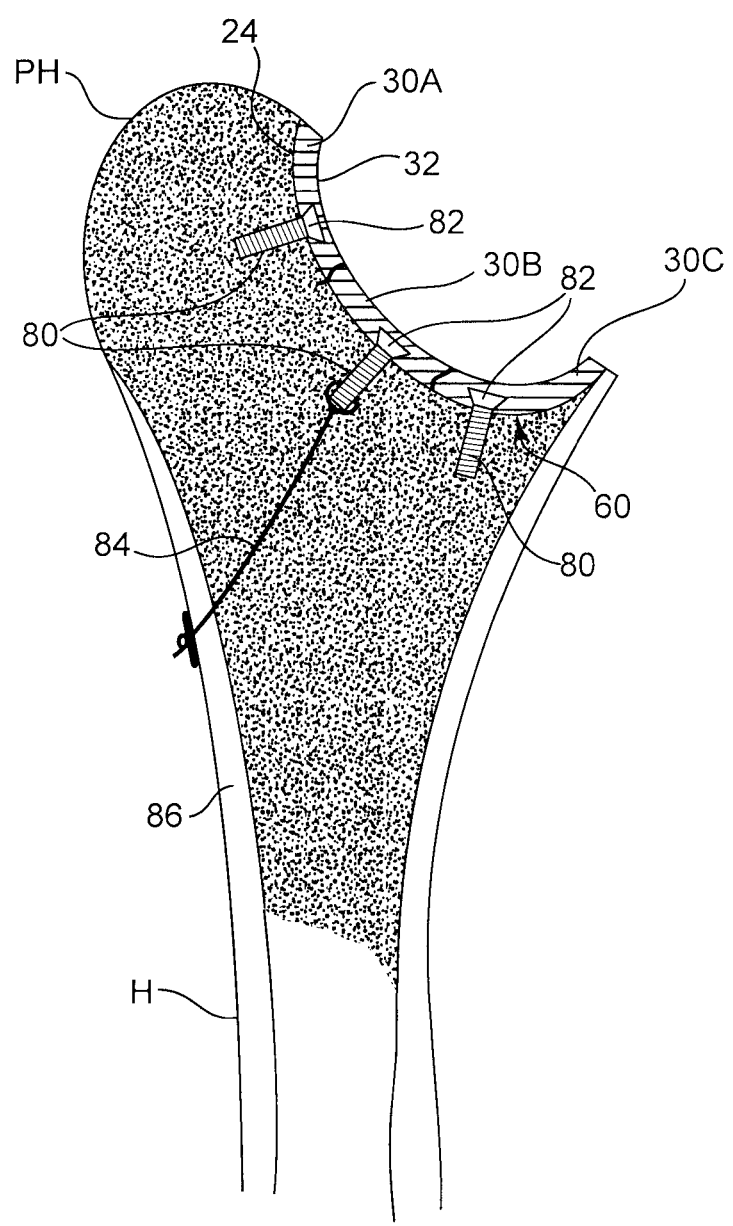
FIG. 7 is a schematic view of a resected portion implanted into a proximal portion of the humerus using fasteners in accordance with an alternate embodiment of the present invention.

FIG. 7 shows a schematic illustration of one embodiment of attaching the articular member 24 to the concave surface 60 of the proximal humerus PH using a plurality of pins 80. The heads 82 of the pins 80 are preferably flush with, or recessed below, the concave inner surface 32. Various bone anchors, known in the art, may also be used in place of the pins 80. The pins 80 may be formed of various materials, including, but not limited to: metallic components and polymeric components. In particular, the pins 80 may be formed of bioresorbable polymers. The pins 80 are particularly useful when the resected portion 30 includes a plurality of pieces 30A, 30B, 30C.

In one embodiment, a suture material 84 is optionally attached to one or more of the pins 80. The suture material 84 extends through the proximal humerus PH to the opposite side and is anchored to the cortical bone 86 using conventional techniques. The suture material 84 operates as a tension member to retain the resected portion 30 to the concave surface 60 of the proximal humerus PH.

Figure 8:
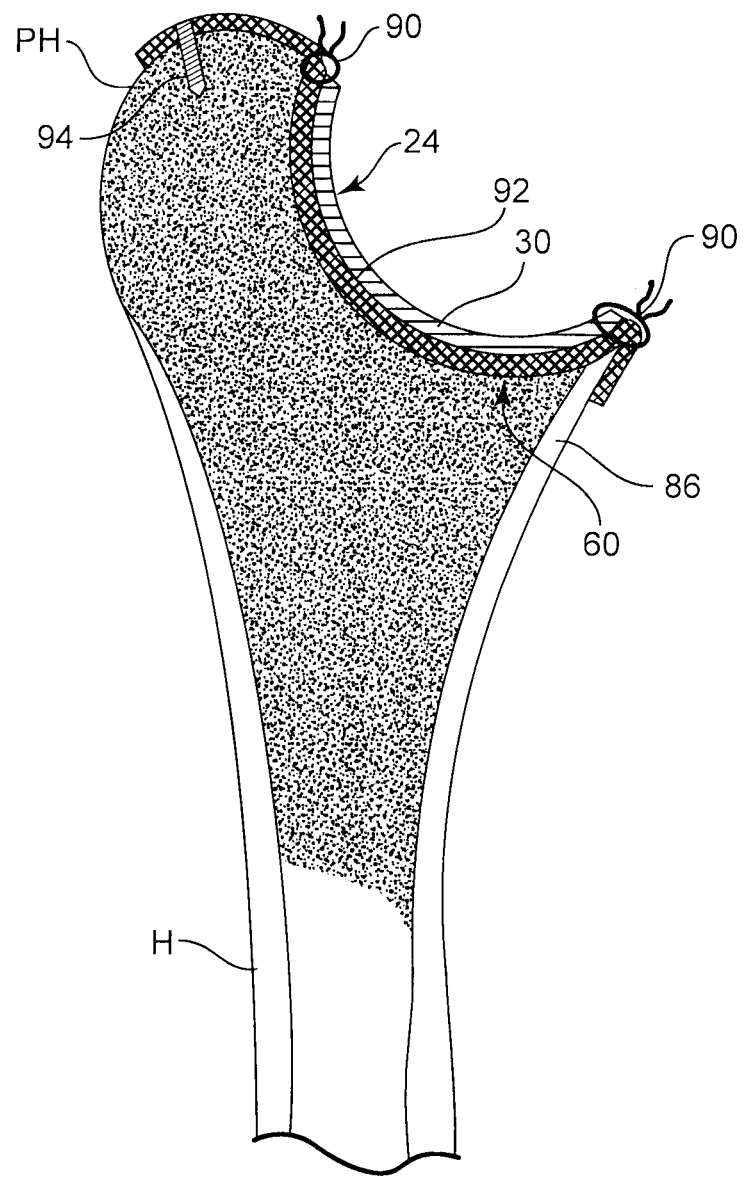
FIG. 8 is a schematic view of a resected portion implanted into a proximal portion of the humerus using sutures in accordance with an alternate embodiment of the present invention.

In an alternate embodiment illustrated in FIG. 8, the resected portion 30 is attached to the proximal humerus PH using a plurality of peripheral sutures 90. The sutures 90 may be formed of various materials, including, but not limited to: metallic components and polymeric components. In particular, the sutures 90 may be formed of bioresorbable polymers. The resected portion 30 may be fixed within the proximal humerus PH by any fixation mechanism, or combination of fixation mechanisms, known in the art without departing from the intended scope of the present invention.

In one embodiment, a reinforcing structure 92, such as for example reinforcing fibers, a three-dimensional porous matrix or scaffold, is located between the concave surface 60 on the proximal humerus PH and the resected portion 30. In the illustrated embodiment, the reinforcing structure 92 is attached to the cortical bone 86 of the proximal humerus PH by the sutures 90. In one embodiment, the reinforcing structure 92 operates like a sling to limit further penetration of the resected portion 30 into the proximal humerus PH. In another embodiment, the reinforcing structure 92 promotes in-growth between the proximal humerus PH and the resected portion 30. Examples of such reinforcing structures include a porous matrix, a scaffold, a reticulated bioceramic framework, a structured porous tantalum and a synthetic fiber mesh. Various porous matrices and scaffoldings are disclosed in U.S. Patent Nos. 4,479,271; 6,511,511; 6,605,117; 6,797,006; 6,902,584; and 7,250,550, which are hereby incorporated by reference. Although the reinforcing structure 92 is discussed as being used in conjunction with the resected portion 30, the reinforcing structure 92 may alternatively be used in place of the resected portion 30 as an articular surface for engaging the interpositional implant 16 (shown in FIGS. 1 and 9).

In another embodiment, the reinforcing structure 92 extends beyond the sutures 90. The reinforcing structure 92 may be made of any material, natural and synthetic, suitable for implantation. Preferably the reinforcing structure 92 is flexible to permit conformity with the proximal humerus PH. The reinforcing structure 92 material may also permit intraoperative cutting or other shaping of the reinforcing structure 92 to fit a surgical site. For example the reinforcing structure 92 may be intraoperatively shapeable by cutting with scissors. The reinforcing structure 92 may include natural tissues including fibrocartilage, fascia, pericardium, and/or other natural tissues. The reinforcing structure 92 may include synthetic materials including metals, polymers, ceramics, hydrogels and/or other suitable materials. A polymer reinforcing structure 92 may include resorbable and/or non-resorbable polymers. Examples of resorbable polymers include polylactic acid polymers, polyglycolic acid polymers, and/or other suitable resorbable polymers. Examples of non-resorbable polymers include polyolefins, polyesters, polyimides, polyamides, polyacrylates, polyketones, and/or other suitable non-resorbable polymers. A metal reinforcing structure 92 may include titanium, tantalum, stainless steel, and/or other suitable metals and alloys thereof. For example metal fibers may be woven into a porous flexible reinforcing structure 92.

The reinforcing structure 92 may be attached to the hard and/or soft tissues of the proximal humerus PH by mechanical fasteners 94, adhesives, tissue in-growth, and/or other suitable attachment mechanism. The attachment mechanism may be permanent and/or bioabsorbable. For example, the reinforcing structure 92 may be screwed, pinned, sutured, or stapled to the bone and/or soft tissue adjacent the joint. The reinforcing structure 92 may include preformed openings for receiving fasteners. The reinforcing structure 92 may include a reinforced edge to strengthen the reinforcing structure 92 against pullout of fasteners. For example, the edge may be reinforced by hemming, molding, braiding, embedding a cord, and/or by other suitable reinforcement mechanism. The reinforced edge may form a thicker portion of the reinforcing structure 92.

Figure 9:
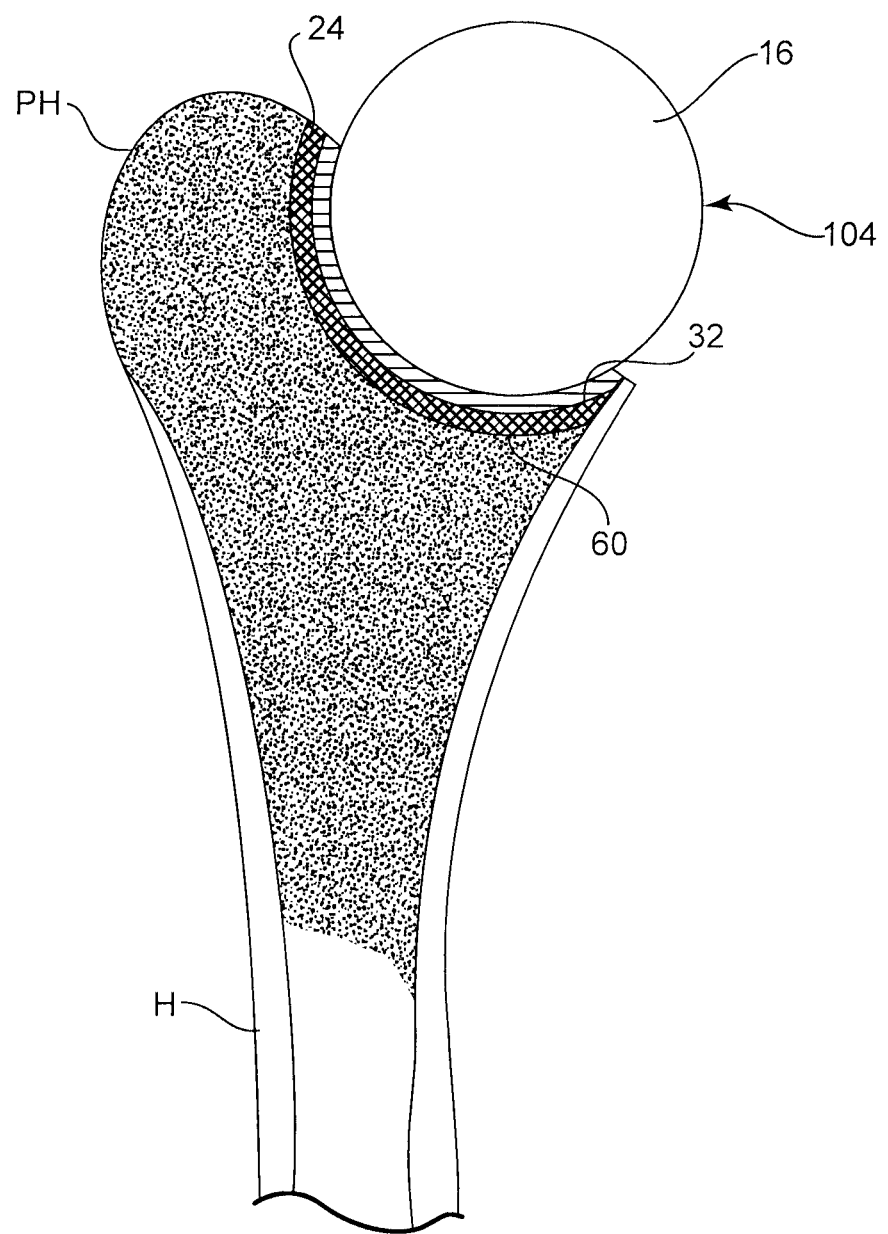
FIG. 9 is a schematic view of an interpositional implant engaged with an implanted resected portion in accordance with the present invention.

FIG. 9 shows the interpositional implant 16 positioned within the articular member 24 at the concave surface 60 of the proximal humerus PH. Referring again also to FIG. 1A, once the articular member 24 is fixed onto the proximal humerus PH or the stem 22 and the articular member 18 is fixed onto the glenoid G, the interpositional implant 16 is positioned between the articular member 24 and the articular member 18. In one embodiment, the interpositional implant 16 is a sphere or ball having a continuous convex surface 104. The interaction of the convex surface 104 of the interpositional implant 16 with the concave articular surface 32 of the articular member 24 and the concave surface 20 of the articular member 18 allows articulation of the prosthesis 10. The size of the interpositional implant 16 is selected such that the convex surface 104 of the interpositional implant 16 is engageable with both the concave surface 20 of the articular member 18 and the concave articular surface 32 of the articular member 24. In one embodiment, the interpositional implant 16 is formed of a polymeric material, metal, ceramic, or a combination thereof. In one embodiment, the interpositional implant 16 is coated with pyrolytic carbon such as that described in U.S. Pat. No. 6,436,146 (Hassler et al.) which is hereby incorporated by reference. Although FIG. 9 depicts the interpositional implant 16 as a sphere, the interpositional implant 16 may have any shape having at least two convex surfaces, such as a disc. The disc may articulate directly with the glenoid G and the humerus H without the need for articular member 18 of glenoid component 12 or articular member 24 of humeral component 14. In another embodiment, the interpositional implant may be replaced by a glenosphere formed of pyrolytic carbon. For example, a convex surface of the glenosphere, or reversed glenoid prosthesis, may be adapted to articulate directly with the reversed, concave surface of the humerus H, and thus eliminate the need for an interpositional implant.

As previously mentioned, the method of resecting natural bone and compacting the resected surface of the natural bone with the resected portion to form a concave articular surface for engagement with a convex articular surface of an interpositional implant to repair or replace a damaged joint is not limited to repairing or replacing a damaged shoulder.

Figure 10:
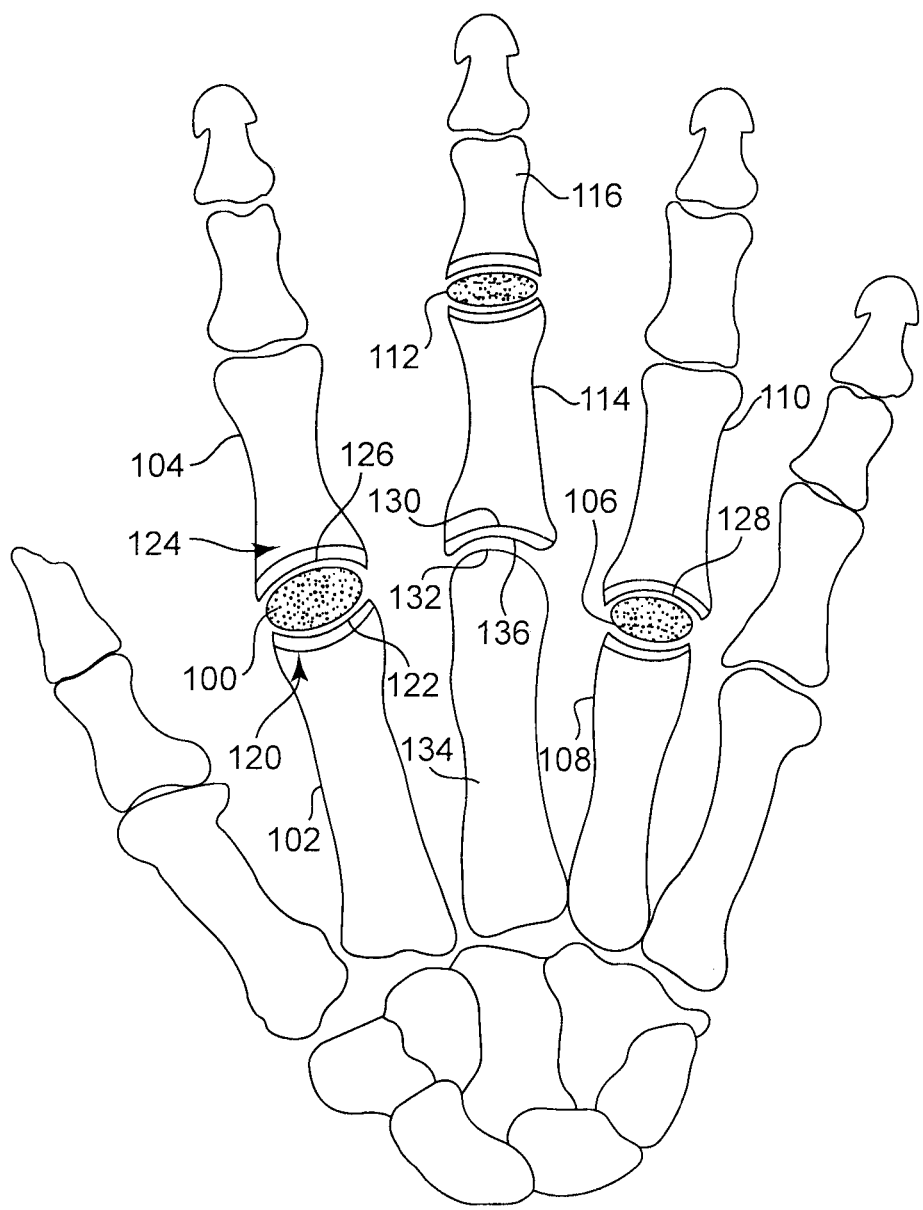
FIG. 10 is a schematic view of intra-articular prostheses implanted in a patient's hand in accordance with an embodiment of the present invention.

FIG. 10 shows a hand having a first interpositional implant 100 implanted between metacarpal 102 and proximal phalange 104. The distal end 120 of the metacarpal 102 is resected and processed in a manner similar to the resection and processing of the glenoid and humeral components 12 and 14 (shown in FIG. 1A) described above, to create a concave articular surface 122. In the illustrated embodiment, the proximal end 124 of the proximal phalange 104 is also resected and processed to create a concave articular surface 126.

FIG. 10 also illustrates a second interpositional implant 106 implanted between metacarpal 108 and proximal phalange 110, and a third interpositional implant 112 implanted between proximal phalange 114 and intermediate phalange 116. The bones 102, 104, 108, 110, 114 and 116 adjacent the respective interpositional implants 100, 106 and 112 are preferably resected and processed in a manner similar to the resection and processing of the glenoid and humeral components 12 and 14 (shown in FIG. 1A) described above. In some embodiments, a natural concave articular surface of one of the bones at the intersection, such as for example on the proximal end 128 of the proximal phalange 110, may be sufficient to retain the interpositional implant 106, making resection unnecessary. The interpositional implants 100, 106 and 112 interact and function with the resected bones in a manner similar to the interpositional implant 16 described above.

In another embodiment, the proximal end 130 of the proximal phalange 114 is resected and processed as discussed herein. The naturally convex surface 132 of the metacarpal 134 engages directly with the concave articular surface 136, without the need for an interpositional implant.

As can be seen in FIG. 10, depending on the joint being repaired or replaced, the shape of the interpositional implants 100, 106 and 112 may be modified so that they are easily implantable between their respective components or bones. Although FIG. 10 depicts interpositional implants between metacarpal bones and proximal phalanges and an interpositional implant between a proximal phalange and a middle phalange, an interpositional implant may be positioned at any joint in the hand, for example, between a middle phalange bone and a distal phalange bone or between the trapezium or scaphoid and a metacarpal bone.

Figure 11:
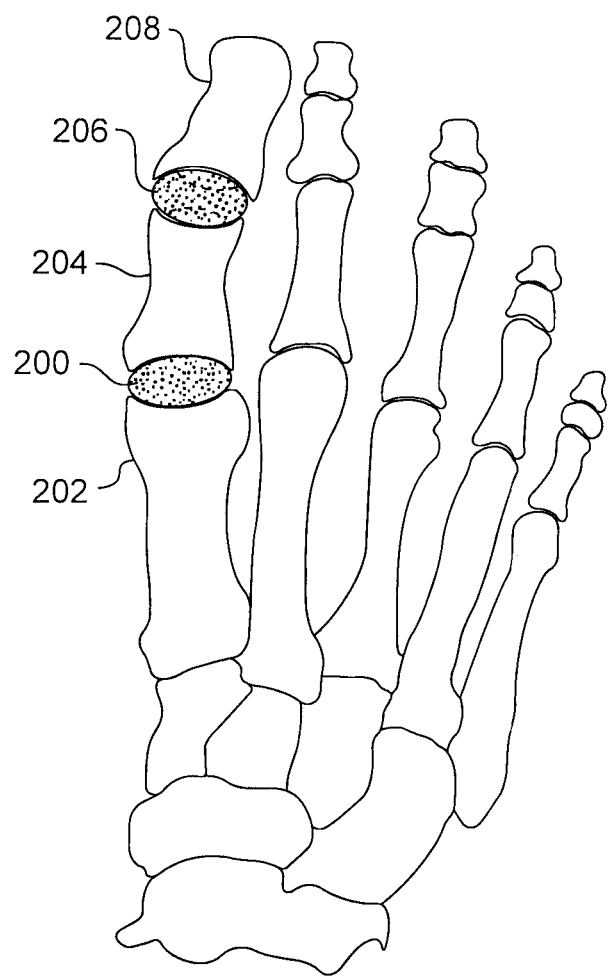
FIG. 11 is a schematic view of intra-articular prostheses implanted in a patient's foot in accordance with an embodiment of the present invention.

FIG. 11 shows a foot having a first interpositional implant 200 implanted between a metatarsal 202 and a proximal phalange 204 and a second interpositional implant 206 implanted between the proximal phalange 204 and a distal phalange 208. The bones 202, 204 and 208 adjacent the respective interpositional implants 200 and 206 are resected and processed in a manner similar to the resection and processing of the glenoid and humeral components 12 and 14 (shown in FIG. 1A) described above. Likewise, the interpositional implants 200 and 206 interact and function with the resected bones in a manner similar to the interpositional implant 16 described above.

Similar to the interpositional implants 100, 106 and 112 depicted in FIG. 10, the shape of the interpositional implants 200 and 206 may be modified so that they correspond to the shape of the resected bone structures within the foot. Although FIG. 11 depicts an interpositional implant between a metatarsal bone and a proximal phalange and an interpositional implant between a proximal phalange and a middle phalange, an interpositional implant may be positioned at any joint in the foot, for example, between a proximal phalange and a middle phalange or between a middle phalange and a distal phalange. Any of the variations disclosed herein can be used with the embodiments of FIGS. 10 and 11, such as for example, the reinforcing structure or fasteners.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of reinforcing an end portion of a first bone of a joint, the method comprising:
   resecting a portion of the end portion of the first bone, thus, resulting in a unitary piece of a resected portion and the end portion of the first bone having a cut surface where the resected portion was removed, wherein the resected portion includes a convex outer surface and an inner cut surface;
   forming a concave recess including a periphery and a concave surface extending from the periphery into the cut surface of the end portion of the first bone;
   positioning a flexible reinforcing structure across at least a portion of the concave recess thus conforming the flexible reinforcing structure to the concave surface of the concave recess;
   attaching the flexible reinforcing structure to the end portion of the first bone along the periphery of the concave recess using a plurality of peripheral sutures;
   preparing the inner cut surface of the resected portion to form an inner concave surface; and
   forming an articular member at the concave surface of the concave recess by impacting the convex outer suface of the resected portion into engagement with the concave surface of the concave recess of the end portion of the first bone so that the convex outer surface is in direct contact with the flexible reinforcing structure and the inner concave surface of the resected portion forms a concave articular suface of the articular member.

2. The method of claim 1, wherein the flexible reinforcing structure comprises a porous matrix, a scaffold, a reticulated bioceramic framework, a structured porous tantalum, a synthetic fiber mesh, or reinforcing fibers.

3. The method of claim 1, further comprising securing an implant having a convex articular surface to a second bone of the joint; and articulating the concave articular surface of the articular member directly with the convex articular surface of the implant.

4. The method of claim 3, wherein the implant is a shoulder implant.

5. The method of claim 3, wherein the end portion of the bone of a joint is a proximal portion of a humerus of a patient's shoulder and the second bone of the joint is a corresponding glenoid of the patient's shoulder.

6. The method of claim 1, wherein preparing the inner cut surface of the resected portion to form an inner concave surface comprises impacting and compressing cancellous bone exposed at the inner cut surface.

7. The method of claim 1, wherein preparing the inner cut surface of the resected portion to form an inner concave surface comprises removing cancellous bone exposed at the inner cut surface.

8. The method of claim 1, wherein the end portion of the bone of a joint is a proximal portion of a humerus of a patient.

* * * * *